United States Patent
Perriello et al.

(10) Patent No.: US 9,192,368 B2
(45) Date of Patent: Nov. 24, 2015

(54) SUSPENSION DEVICE TO ANCHOR TISSUE GRAFT

(75) Inventors: Michael James Perriello, Hopedale, MA (US); Alfred Rodrigue Berube, Jr., North Attleboro, MA (US); Michael Charles Ferragamo, Foster, RI (US)

(73) Assignee: Smith & Nephew, Inc., Memphis, TN (US)

( * ) Notice: Subject to any disclaimer, the term of this patent is extended or adjusted under 35 U.S.C. 154(b) by 172 days.

(21) Appl. No.: 13/198,421

(22) Filed: Aug. 4, 2011

(65) Prior Publication Data

US 2013/0035720 A1 Feb. 7, 2013

(51) Int. Cl.
*A61B 17/04* (2006.01)
*A61F 2/08* (2006.01)

(52) U.S. Cl.
CPC .......... *A61B 17/0401* (2013.01); *A61F 2/0811* (2013.01); *A61B 17/0487* (2013.01); *A61B 2017/0404* (2013.01); *A61B 2017/0496* (2013.01); *A61F 2002/0852* (2013.01); *A61F 2002/0864* (2013.01); *A61F 2002/0882* (2013.01)

(58) Field of Classification Search
USPC ............... 606/144, 228, 215, 232; 623/13.13, 623/13.14, 13.19
See application file for complete search history.

(56) References Cited

U.S. PATENT DOCUMENTS

| | | | |
|---|---|---|---|
| 5,306,301 A | 4/1994 | Graf et al. | |
| 5,769,894 A | 6/1998 | Ferragamo | |
| 5,879,371 A | 3/1999 | Gardiner et al. | |
| 6,296,659 B1 | 10/2001 | Foerster | |
| 6,517,578 B2 | 2/2003 | Hein | |
| 6,902,573 B2 | 6/2005 | Strobel et al. | |
| 6,972,027 B2 | 12/2005 | Fallin et al. | |
| 6,994,725 B1* | 2/2006 | Goble | 623/13.14 |
| 7,090,690 B2* | 8/2006 | Foerster et al. | 606/232 |
| 7,491,217 B1* | 2/2009 | Hendren et al. | 606/232 |
| 7,594,923 B2 | 9/2009 | Fallin et al. | |
| 7,819,898 B2 | 10/2010 | Stone et al. | |
| 7,875,058 B2 | 1/2011 | Holmes | |
| 8,100,923 B2* | 1/2012 | Paraschac et al. | 606/148 |
| 2001/0008971 A1 | 7/2001 | Schwartz et al. | |
| 2001/0041938 A1 | 11/2001 | Hein | |

(Continued)

FOREIGN PATENT DOCUMENTS

NL 1028292 8/2006
WO 01/56507 8/2001

OTHER PUBLICATIONS

International Search Report in corresponding PCT Application No. PCT/US2012/048037 filed Jul. 25, 2012.

*Primary Examiner* — Tuan V Nguyen
(74) *Attorney, Agent, or Firm* — Burns & Levinson LLP; Joseph M. Maraia (57) ABSTRACT

A tissue graft suspension device includes a platform member defining an opening, a suture having a first portion and a second portion, and a fixation member mating with the opening in the platform member. The first portion and the second portion pass through the opening such that a third portion of the suture forms a loop for attachment to a tissue graft. The fixation member includes a retaining mechanism configured to allow the first portion or the second portion to pass through the opening in a manner that decreases a size of the loop and to prevent the first portion or the second portion of the suture from passing through the opening in a manner that increases a size of the loop.

8 Claims, 8 Drawing Sheets

(56) References Cited

U.S. PATENT DOCUMENTS

| | | |
|---|---|---|
| 2002/0161439 A1 | 10/2002 | Strobel et al. |
| 2004/0002734 A1 | 1/2004 | Fallin et al. |
| 2004/0098050 A1* | 5/2004 | Foerster et al. ............... 606/232 |
| 2005/0143762 A1* | 6/2005 | Paraschac et al. ............ 606/148 |
| 2005/0277961 A1 | 12/2005 | Stone et al. |
| 2006/0142769 A1* | 6/2006 | Collette .......................... 606/73 |
| 2006/0282081 A1* | 12/2006 | Fanton et al. .................... 606/72 |
| 2007/0162125 A1* | 7/2007 | LeBeau et al. ............. 623/13.14 |
| 2007/0239209 A1 | 10/2007 | Fallman |
| 2008/0208252 A1 | 8/2008 | Holmes |
| 2008/0312689 A1 | 12/2008 | Denham et al. |
| 2010/0256677 A1 | 10/2010 | Albertorio et al. |
| 2010/0262185 A1 | 10/2010 | Gelfand et al. |
| 2011/0022061 A1 | 1/2011 | Orphanos et al. |
| 2012/0123541 A1 | 5/2012 | Albertorio et al. |

\* cited by examiner

SUSPENSION DEVICE TO ANCHOR TISSUE GRAFT

TECHNICAL FIELD

This document relates to tissue graft anchoring.

BACKGROUND

An anterior cruciate ligament (ACL) that has ruptured and is non-repairable is generally replaced arthroscopically by a tissue graft. The tissue graft can be harvested from a portion of a patellar tendon having so called "bone blocks" at each end, and from the semitendonosis and gracilis. Alternatively, the tissue graft can be formed from synthetic materials or from a combination of synthetic and natural materials.

The replacement tissue graft is implanted by securing one end of the tissue graft in a socket formed in a passage within the femur, and passing the other end of the graft through a passage formed in the tibia. Generally, sutures are used to affix each end of the tissue graft to a fastener (e.g., an interference screw or a post), which is then secured to the bone.

A graft fixation member, e.g., a fixation button, can be used to secure the tissue graft at the femoral cortex, as described in U.S. Pat. No. 5,306,301 ("the '301 patent") hereby incorporated by reference in its entirety. When using a fixation button, the femoral passage generally includes a relatively larger diameter portion for receiving the graft, and a smaller diameter, passing channel near the femoral cortex for receiving a length of suture that runs from the tissue graft to the fixation button. By measuring the total length of the femoral passage and the length of the larger diameter portion of the femoral passage, the surgeon determines the appropriate length of suture material for attaching the fixation button to the tissue graft.

SUMMARY

According to one aspect, a tissue graft suspension device includes a platform member defining an opening, a suture having a first portion and a second portion, and a fixation member mating with the opening in the platform member. The first portion and the second portion pass through the opening such that a third portion of the suture forms a loop for attachment to a tissue graft. The fixation member includes a retaining mechanism configured to allow the first portion or the second portion of the suture to pass through the opening in a manner that decreases a size of the loop and to prevent the first portion or the second portion of the suture from passing through the opening in a manner that increases a size of the loop.

Implementations of this aspect may include one or more of the following features.

The fixation member is configured to slide through the opening in the platform member. The retaining mechanism includes a first wedge and a second wedge. The platform member includes a first groove and a second groove. The first portion of the suture passes through the first groove and the second portion of the suture passes through the second groove. The first wedge engages with the first groove such that the first portion of the suture is able to move in a first direction that decreases the size of the loop but is prevented from moving in a direction opposite the first direction to increase the size of the loop. The second wedge engages with the second groove such that the second portion of the suture is able to move in a second direction that decreases the size of the loop but is prevented from moving in a direction opposite the second direction to increase the size of the loop. The first wedge and the second wedge each include a tapered structure. The first wedge and the second wedge each include at least one step member. The first wedge and the second wedge are at a first end of the fixation member. A passage is at a second end of the fixation member opposite from the first end. The first portion of the suture and the second portion of the suture pass through the passage such that a force exerted on the loop causes the first wedge to engage the first groove and the second wedge to engage the second groove. The platform member includes a second opening and a third opening, each to receive a respective end of the suture that is passed through the opening. A length of the fixation member is greater than a thickness of the platform member such that the passage at the second end extends beyond a bottom surface of the platform member.

According to another aspect, a tissue graft suspension device includes a bushing member defining an opening, a suture having a first portion and a second portion, and a fixation member mating with the opening in the bushing member. The first portion and the second portion pass through the opening such that a third portion of the suture between the first portion and the second portion connects the bushing member to a platform member. The fixation member includes a retaining mechanism configured to allow the first portion or the second portion of the suture to pass through the opening in a manner that decreases a length of the third portion and to prevent the first portion or the second portion from passing through the opening in a manner that increases the length of the third portion.

Implementations of this aspect may include one or more of the following features.

The fixation member is configured to slide through the opening in the bushing member. The retaining mechanism includes a first wedge and a second wedge. The bushing member includes a first groove and a second groove. The first portion of the suture passes through the first groove and the second portion of the suture passes through the second groove. The first wedge engages with the first groove such that the first portion of the suture is able to move in a direction that decreases the length of the third portion but is prevented from moving in a direction opposite the first direction to increase the length of the third portion. The second wedge engages with the second groove such that the second portion of the suture is able to move in a second direction that decreases the length of the third portion but is prevented from moving in a direction opposite the second direction to increase the length of the third portion. The first wedge and the second wedge each include a tapered structure. The first wedge and the second wedge each include at least one step member. A first passage is at a first end of the fixation member. The third portion of the suture passes through the first passage. A second passage is at a second end of the fixation member opposite from the first end. The second passage can receive another suture for attachment to a tissue graft. The first wedge and the second wedge are between the first passage and the second passage. The first portion of the suture and the second portion of the suture pass through the first passage such that a force on the bushing member exerted away from the platform member causes the first wedge to engage the first groove and the second wedge to engage the second groove. A length of the fixation member is greater than a thickness of the bushing member such that the first passage extends beyond a bottom surface of the bushing member and the second passage extends beyond a top surface of the bushing member. The platform member includes a second opening and a third opening, each to receive a respective end of the suture that is passed through the opening.

According to yet another aspect, a method of securing a tissue graft includes providing a platform member having a suture attached thereto. The suture has a first portion and a second portion. The first portion and the second portion pass through an opening defined in the platform member such that a third portion of the suture forms a loop for attachment to a tissue graft. The method includes providing a fixation member to mate with the opening in the platform member. The fixation member includes a retaining mechanism configured to allow the first portion or the second portion of the suture to pass through the opening in a manner that decreases a size of the loop and to prevent the first portion or the second portion of the suture from passing through the opening in a manner that increases a size of the loop. The method includes attaching the loop to the tissue graft, and adjusting the size of the loop by pulling the first portion or the second portion through the opening in the manner that decreases the size of the loop.

Implementations of this aspect may include one or more of the following features.

The platform member, the suture, the fixation member, and attached tissue graft are passed through a bone passage. Then, the size of the loop is adjusted.

According to a further aspect, a method of securing a tissue graft includes providing a bushing member having a suture attached thereto, the suture having a first portion and a second portion, the first portion and the second portion passing through an opening defined in the bushing member such that a third portion of the suture between the first portion and the second portion connects the bushing member to a platform member. The method includes providing a fixation member to mate with the opening in the bushing member, the fixation member including a retaining mechanism configured to allow the first portion or the second portion of the suture to pass through the opening in a manner that decreases a length of the third portion and to prevent the first portion or the second portion from passing through the opening in a manner that increases the length of the third portion. The method includes attaching another suture to the fixation member, attaching the other suture to a tissue graft, and adjusting the length of the third portion by causing the first portion or the second portion to pass through the opening in the manner that decreases the length of the third portion.

Implementations of this aspect may include passing the suture through openings defined in the platform member, and passing the platform member, the suture, the bushing member, and the fixation member through a bone passage, followed by adjusting the length of the third portion.

The details of one or more implementations are set forth in the accompanying drawings and the description below. Other features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

This document describes an example of a suspension device to anchor tissue grafts. The suspension device can, for example, be used to fixate tissue grafts, such as soft tissue and bone-tendon grafts, in a tunnel within a cortical bone layer of a bone. In some implementations, a distance from the cortical bone to the tissue graft can be adjusted, for example, while the suspension device and the tissue graft are in the tunnel. In some situations, the distance can be reduced to less than 15 mm, for example, to 0 mm.

Figure 1A:
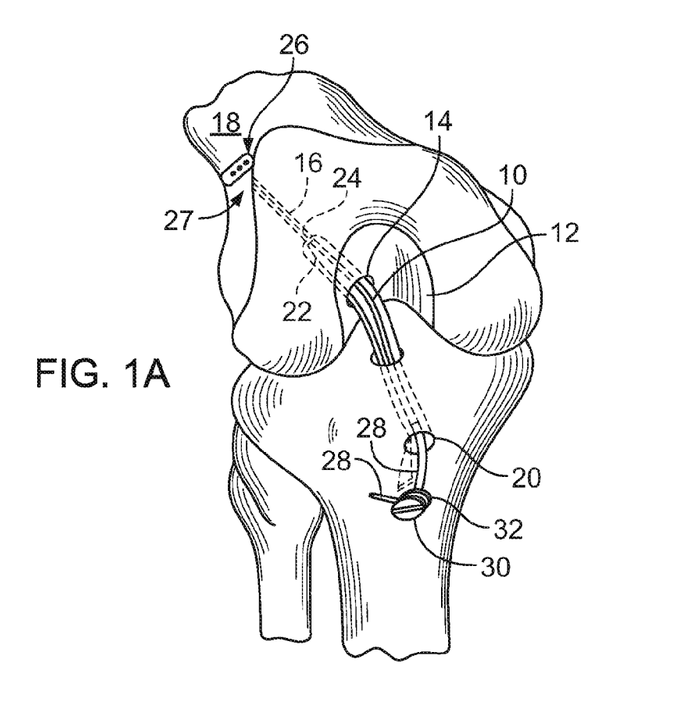
FIGS. 1A and 1B are illustrations of a tissue graft secured within the knee by a graft suspension device.
Figure 1B:
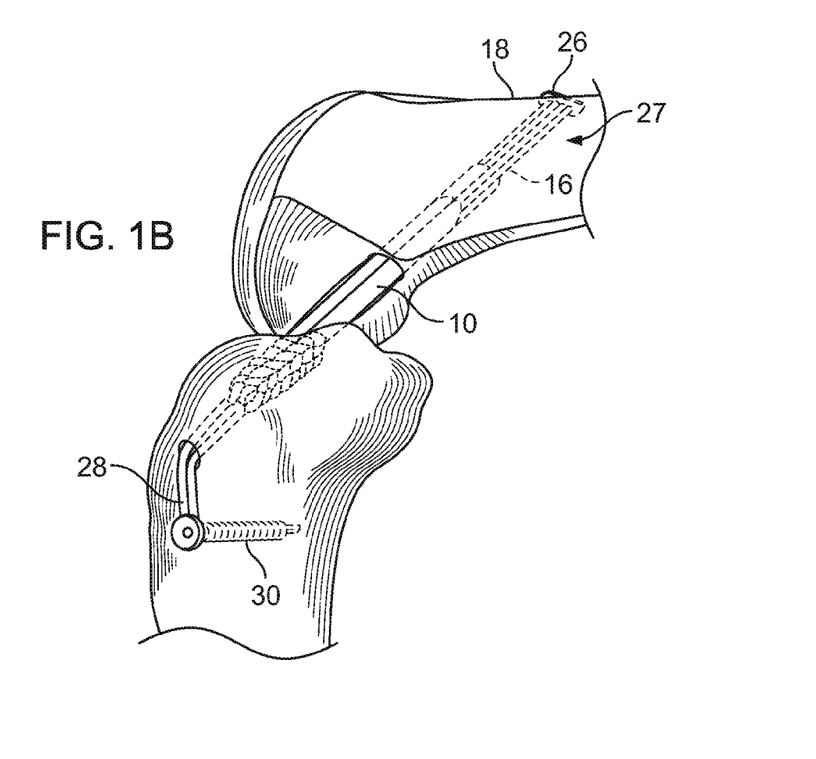

Referring to FIGS. 1A and 1B, a knee joint has a tissue graft 10 (e.g., a patellar tendon graft (FIG. 1A) or a semitendonosis and gracilis graft (FIG. 1B)) implanted in an anterior cruciate ligament (ACL) repair and reconstruction procedure. Prior to implanting tissue graft 10, a notchplasty procedure is preferably performed to expand the intercondylar notch 12 of the femur bone. A femoral channel 14 for receiving one end of tissue graft 10 is then drilled from notch 12 a predetermined distance within the femur with a passing channel 16 of reduced diameter drilled further through the femur from femoral channel 14 to a region of femoral cortex 18. A tibial channel 20 for receiving the other end of tissue graft 10 is drilled from an anterior region of the tibia to a region near the opening of femoral channel 14.

In the case of patellar tendon graft, one end of tissue graft 10 includes a bone block 22 which is shaped and sized in close conformity with femoral channel 14 to ensure optimal healing. A length of suture 24 has one end attached to bone block 22 and the other end secured at femoral cortex region 18 with a suspension device 26. The suture 24 is a woven or braided suture, for example, #5 Ultrabraid suture, attached to the suspension device 26 in a loop configuration. In some implementations described below, the suspension device 26 is configured to receive the tissue graft 10 in the loop, and to maintain a distance between the tissue graft 10 and the suspension device 26, for example, by preventing an increase in a length of the suture 10 in response to a force of the tissue graft 10 away from the suspension device 26. The other end of tissue graft 10 includes a second length of suture 28 which is attached to the tibia, for example, with a fixation screw 30. A washer 32 either attached to or positioned under the head of fixation screw 30 helps in holding the suture in place when screw 30 is tightened.

Figure 2:
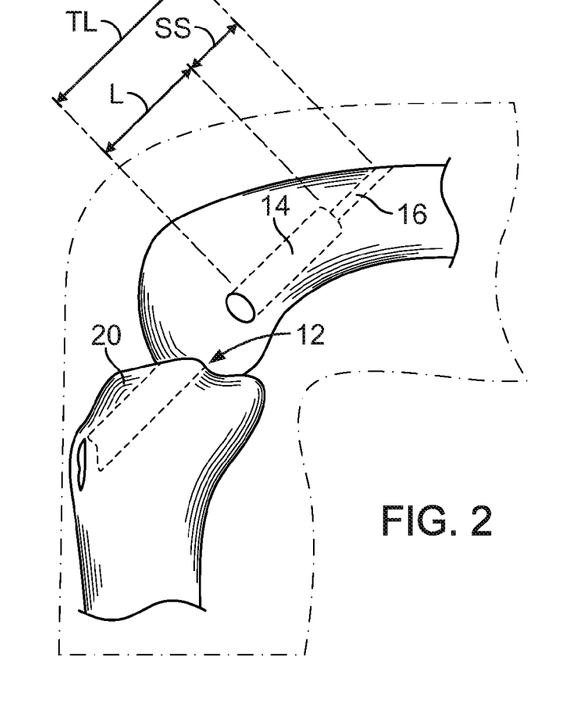
FIG. 2 is another view of the knee joint of FIG. 1.

Referring to FIG. 2, length (L) of femoral channel 14 is selected by the surgeon in accordance with the length of bone block 22 and the desired insertion distance of tissue graft 10 within the femur. The span of suture 24, designated as SS, is approximately that of passing channel 16 so that the sum of the desired insertion length (L) and span of suture (SS) is the measured total length (TL) from the opening of femoral channel 14 to the opening at femoral cortex 18. Each of these dimensions is measured prior to implanting the tissue graft so that during the implantation procedure, the surgeon, under arthroscopic observation, can be assured that tissue graft 10 has been properly positioned within femoral channel 14.

The ability to adjust the length of the suture 24 allows the length of the suture span (SS) to be minimized, only being limited by the desired length of passing channel 16. Once the suspension device 26 is located against the femoral cortex 18, the tissue graft 10 can be positioned at a desired distance from the suspension device 26 by pulling on the ends of the suture 24, and the distance can be maintained by an interaction between the suture 24 and a retaining mechanism described below.

Figure 3A:
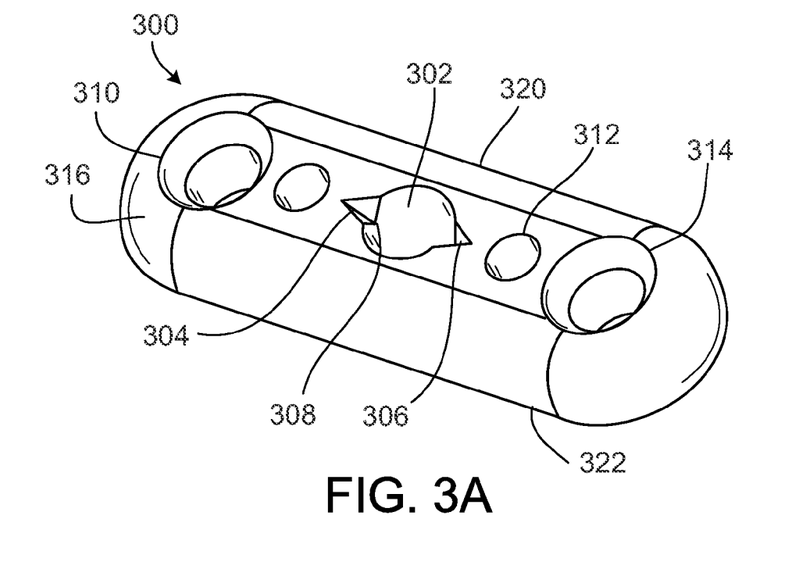
FIG. 3A is a perspective view of an example of a platform member.
Figure 3B:
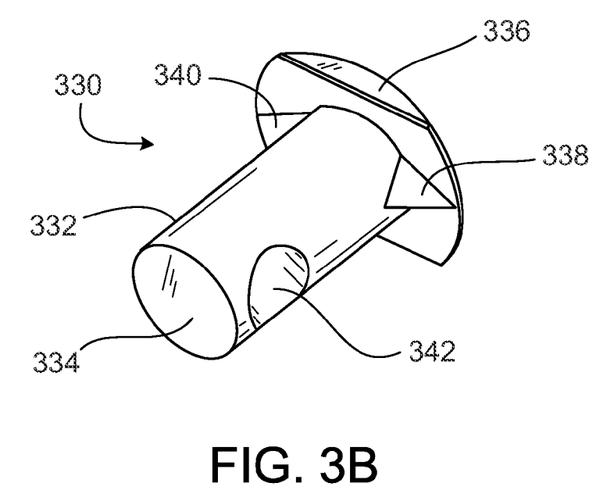
FIG. 3B is a perspective view of an example of a fixation member.
Figure 3C:
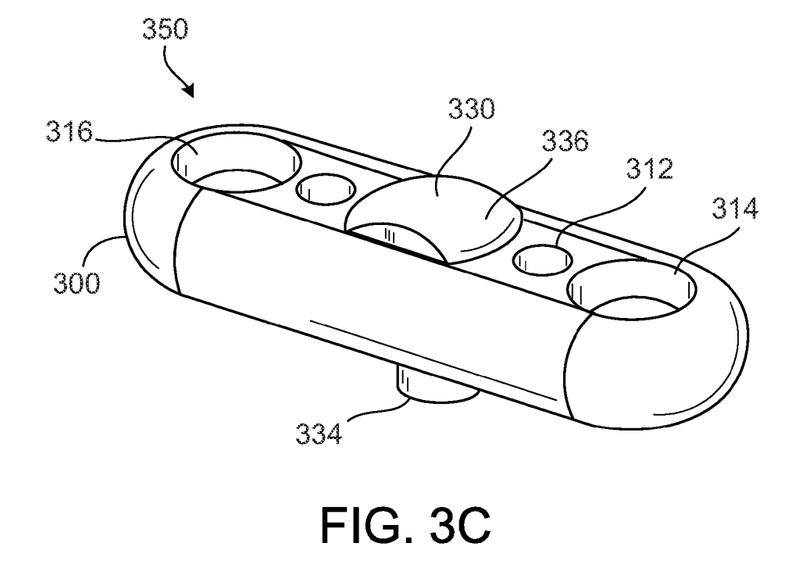
FIG. 3C is a perspective view of the platform member of FIG. 3A mated with the fixation member of FIG. 3B.

FIGS. 3A, 3B, and 3C are perspective views of examples of components 300 and 330 of a suspension device 350 that can be used, for example, as the suspension device 26. As described below, the components 300 and 330 are configured to allow the suspension device to receive portions of a suture formed as an adjustable loop for attachment of a tissue graft, and to allow one or more portions of the suture to pass through in a manner that permits a decrease in the size of the loop but prevents an increase in the size. By doing so, the suspension device 350 enables adjusting and maintaining a distance between the tissue graft and the suspension device 350.

Figure 4A:
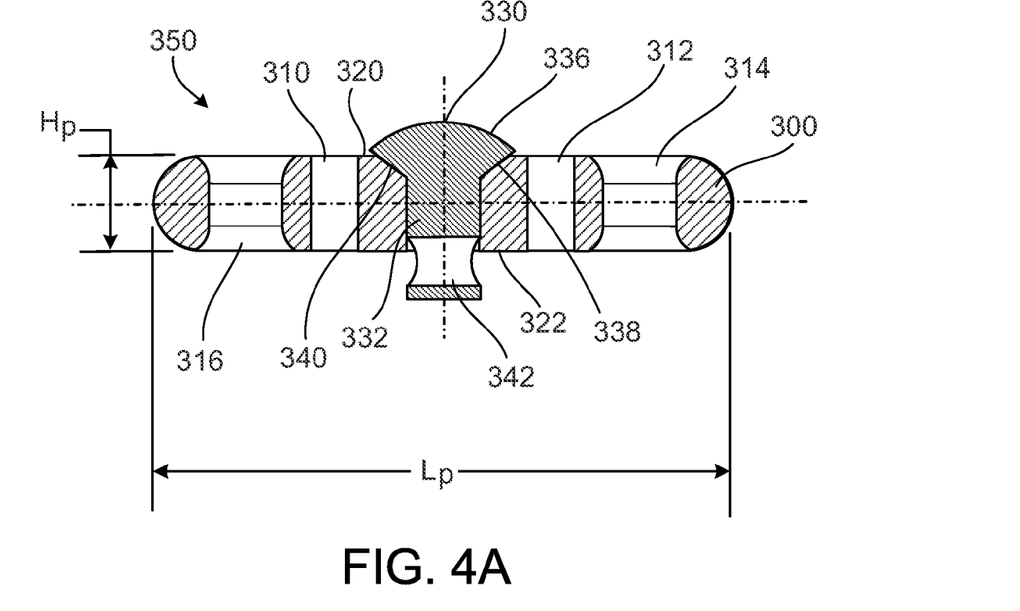
FIG. 4A is a cross-sectional view of the platform member and the fixation member in a locked position.
Figure 4B:
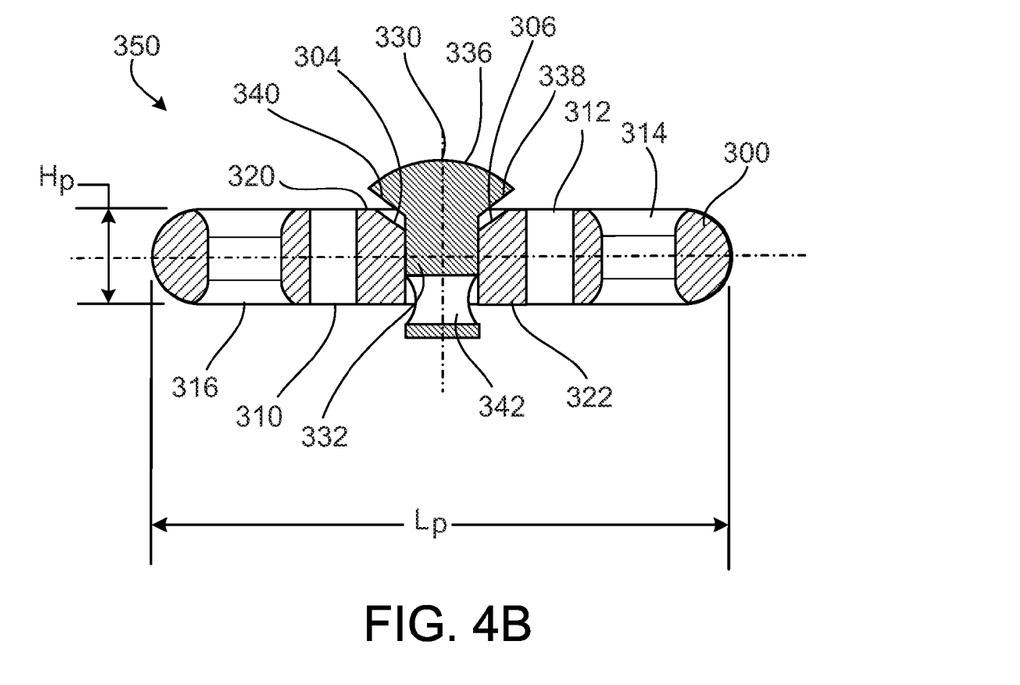
FIG. 4B is a cross-sectional view of the platform member and the fixation member in an unlocked position.

The suspension device 350 includes a platform member 300 (FIG. 3A) having a length ($L_p$, for example, 12 mm), a width ($W_p$, for example, 4 mm), and a height ($H_p$, for example, 1.5 mm) (FIGS. 4A and 4B). The platform member 300 includes an opening 302 through which portions of the suture for attachment to the tissue graft are passed. The opening 302 is formed at a center of a top surface 320 of the platform member 300, and spans the height of the platform member 300 from the top surface 320 to a bottom surface 322. An axis of the opening 302 is perpendicular to the top surface 320 and the bottom surface 322 of the platform member 300, although the axis may not be perpendicular in other implementations. The opening 302 has a circular cross-section (for example, with a diameter of 2 mm), but in other implementations the opening 302 can have other cross-sections, for example, rectangular or elliptical.

The platform member 300 includes grooves, for example, a first groove 304 and a second groove 306, to receive respective portions of the suture passed through the opening 302. The first groove 304 and the second groove 306 are formed on diametrically opposite ends of a circumference of the opening 302 adjacent the top surface 320 of the platform member. In particular, the first groove 304 and the second groove 306 are formed partially on the top surface 320 of the platform member 300 and partially in an inner surface 308 of the platform member 300 that defines the opening 302. Each groove is tapered to receive a tapered wedge 340 and 338, described below.

Figure 5:
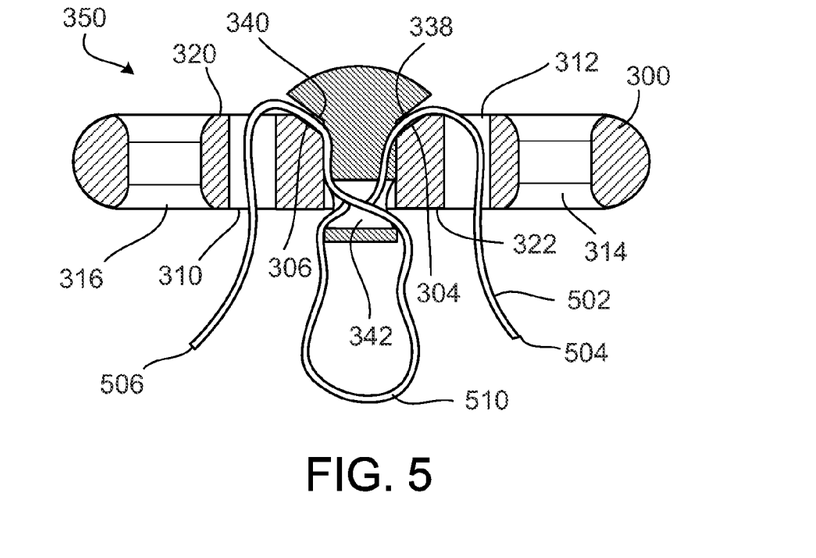
FIG. 5 is a cross-sectional view of the platform member and the fixation member with a suture forming a loop to attach a tissue graft.

The platform member 300 includes a second opening 310 and a third opening 312 formed, for example, on either side of the opening 302. The respective ends of the suture that are passed through the opening 302 and along the first groove 304 and the second groove 306 are passed through the second opening 310 and the third opening 312, respectively (FIG. 5). The second opening 310 and the third opening 312 are formed such that a line connecting the edges of the two grooves is collinear with a line connecting the centers of the second opening 310 and the third opening 312. Both lines are parallel to an axis of the platform member 300 along the length, $L_p$.

Each of the second opening 310 and the third opening 312 span the height of the platform member 300 from the top surface 320 to the bottom surface 322. An axis of each opening is perpendicular to the top surface 320 and the bottom surface 322, although the axis may not be perpendicular in other implementations. Also, each of the second opening 310 and the third opening 312 has a circular cross-section, while in other implementations each opening may have a rectangular cross-section, an elliptical cross-section, or the like. In some situations, the second opening 310 and the third opening 312 are formed to have the same cross-sectional dimension, which is smaller than that of the first opening 302.

The platform member 300 also includes an additional pair of openings (for example, a fourth opening 314 and a fifth opening 316) to secure the platform member 300 to the femoral cortex 18. The fourth opening 314 and the fifth opening 316 are positioned on either side of the opening 302, similarly to the second opening 310 and the third opening 312, respectively. In particular, the fourth opening 314 and the fifth opening 316 are formed adjacent respective ends of the platform member 300 along the width, $W_p$, of the platform member 300. The fourth opening 314 and the fifth opening 316 are formed to have the same cross-sectional dimension, which is greater than the cross-sectional dimension of the second opening 310 and the third opening 312.

The suspension device includes a fixation member 330 (FIG. 3B) that mates with the opening 302 in the platform member 300. As described below, the fixation member 330 includes a retaining mechanism configured to allow one or more portions of the suture to pass through the opening 302 in a manner that decreases a size of the loop and to prevent the one or more portions of the suture from passing through the opening 302 in a manner that increases a size of the loop.

The retaining mechanism includes a first wedge 338 and a second wedge 340 attached to an outer surface 332 of the fixation member 330. The first wedge 338 and the second wedge 338 are formed near a top end 336 on diametrically opposite sides of the fixation member 330. Each wedge includes a tapered structure that mates with a respective groove that is formed partially on the top surface 320 of the platform member 300 and partially in an inner surface 308 of the platform member 300 that defines the opening 302. The fixation member 330 includes a passage 342 (for example, a hole) at a bottom end 334 of the fixation member 330 opposite from the top end 336. An axis of the passage 342 is perpendicular to the axis of the fixation member 330, while in other implementations, the axis of the passage 342 may not be perpendicular to the axis of the fixation member 330. In addition, the axis of the passage 342 is aligned with a straight line passing through the edges of the first wedge 338 and the second wedge 340. A size of the passage 342 is sufficient for portions of the suture to pass through and can be, for example, 1 mm.

The fixation member 330 mates with the platform member (FIG. 3C) when the fixation member 330 is slid through the opening 302 such that the first wedge 338 and the second wedge 340 align with the first groove 304 and the second groove 306, respectively. The fixation member 330 has a cylindrical body with a diameter, for example, of 1.5 mm. A top end 336 of the fixation member 330 is formed to have a cross-sectional dimension greater than that of the opening 302 to prevent the fixation member 330 from sliding out of the opening 302. In addition, a length of the fixation member 330 is greater than a height of the platform member 300 such that the passage 342 at the bottom end 334 extends beyond a bottom surface 322 of the platform member 300 to permit inserting portions of the suture into the passage 342 after sliding the fixation member 330 through the opening 302. For example, the length of the fixation member is 3 mm.

FIGS. 4A and 4B are each a cross-sectional view of the platform member 300 and the fixation member 330 in a locked position and in an unlocked position, respectively. In a locked position (FIG. 4A), the first wedge 338 engages with the first groove 304 and the second wedge 340 engages with the second groove 306. Specifically, to lock the fixation member 330 in the platform member 300, the first wedge 338 is aligned with the first groove 304, the second wedge 340 is aligned with the second groove 306, and the fixation member 330 is pushed into the opening 302 until the top end 336 of the fixation member 300 is as close to the top surface 320 of the platform member 300 as possible. In an unlocked position (FIG. 4B), the first wedge 338 disengages from the first groove 304 and the second wedge 340 disengages from the second groove 306 when the fixation member 330 is pulled away from the opening 302.

FIG. 5 is a cross-sectional view of the suspension device 350 with a suture 502 forming a loop 510 to attach a tissue graft (not shown). To load the suture 502, the fixation member 330 can be slid into the opening 302 of the platform member 300 as shown in FIG. 5. A first portion 504 of the suture 502 can be passed through an end of the passage 342 and a second portion 506 of the suture 502 can be passed through an opposite end of the passage 342 to form a loop 510. The first portion 504 and the second portion 506 can then be passed through the opening 302 and pulled out of the opening 302 at the top surface 320. The first portion 504 and the second portion 506 can then be passed through the second opening 310 and the third opening 312, respectively. The fixation member 330 can then be placed in the locked position in which the first wedge 338 and the second wedge 340 engage with the first groove 304 and the second groove 306, respectively.

In some implementations, the fixation member 330 can be pre-loaded with the suture 502. In such implementations, the first portion 504 and the second portion 506 of the suture 502 can be passed through the passage 342, as described above, before sliding the fixation member 330 into the opening 302. In use, a surgeon need not perform any operation to assemble the suspension device 350. Instead, the surgeon may use the suspension device 350 by passing the graft through the loop 510.

When the fixation member 330 is in the locked position, the wedges 338 and 340 allow the first portion 504 or the second portion 506 of the suture 502 to pass through the opening 302 in a manner that decreases a size of the loop 510, but prevent the first portion 504 or the second portion 506 of the suture 510 from passing through the opening 302 in a manner that increases a size of the loop 510. For example, the first portion 504 of the suture 502 that passes through the first groove 338 and the second opening 310 is able to move in a direction from the top surface 320 of the platform member 300 toward the bottom surface 322 of the platform member 300 but not in an opposite direction in part because of the interaction between the first edge 338 and the first groove 304. In addition, a downward force exerted on the loop 510 results in the loop 510 exerting a downward force on the fixation member 330, causing the first wedge 338 to further engage the first groove 304 and the second wedge 340 to further engage the second groove 306. Consequently, in the locked position, a size of the loop 510 formed in the suture 502, and a distance between a tissue graft (not shown) attached to the loop 510 and the platform member 300 is maintained.

In operation, a surgeon can attach the loop to the tissue graft, and adjust the size of the loop by pulling the first portion 504 or the second portion 506 through the opening 302 in a manner that decreases the size of the loop 510. Specifically, the surgeon can pass the platform member 300, the suture 502, the fixation member 330, and the attached tissue graft through a bone passage and then adjust the size of the loop 510.

Figures 6A, 6B:
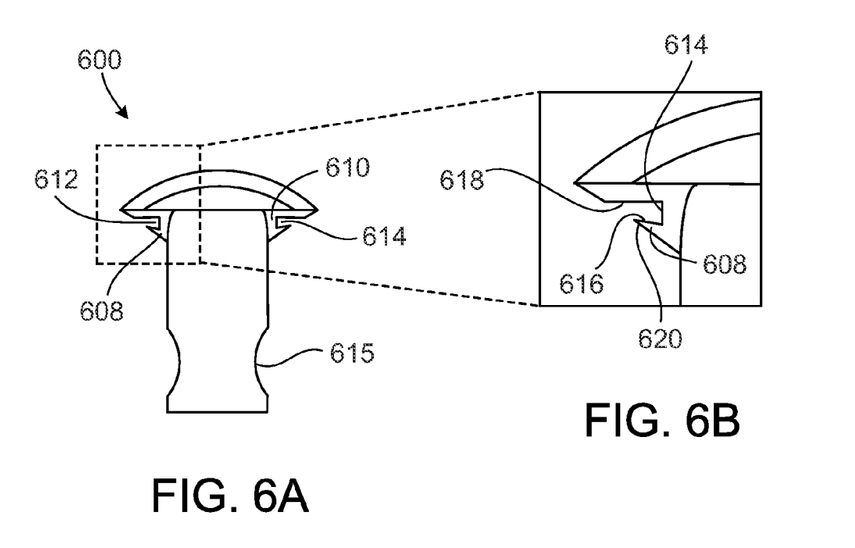
FIGS. 6A and 6B are side views of an example of a fixation member including at least one step member.

FIGS. 6A and 6B are side views of a fixation member 600 including at least one step member. The fixation member 600 shown in FIG. 6A is substantially similar to the fixation member 330, and includes a first wedge 608 and a second wedge 610. A recess (for example, a first recess 612 and a second recess 614) can be formed in each wedge. For example, the recess 614 is cut on a side surface 620 of the wedge 608 to form steps 616 and 618 (FIG. 6B). When a portion of a suture (not shown) is passed through the passage 615 and past a groove with which the wedge 608 or 610 engages, the step member formed by the recess 612 or 614 engages with the portion of the suture such that the portion can pass in one direction but not in the opposite direction, as described above.

Figure 8:
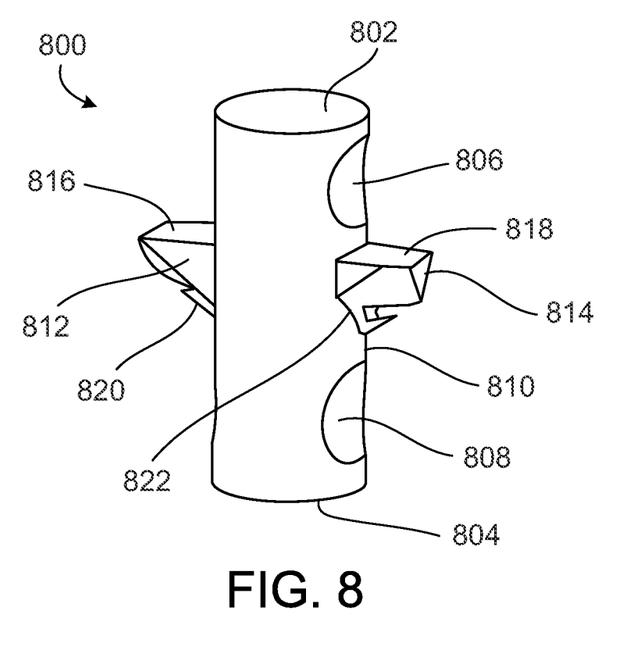
FIG. 8 is a perspective view of an example of a fixation member designed to mate with the bushing member.
Figure 9:
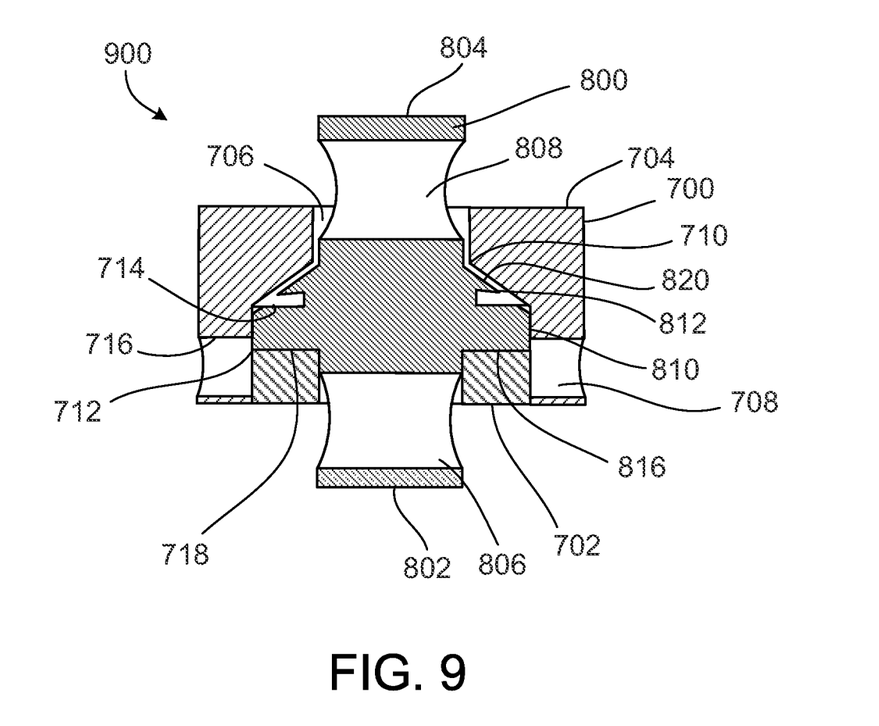
FIG. 9 is a cross-sectional view of the fixation member of FIG. 8 mated with the bushing member of FIG. 7.
Figure 10:
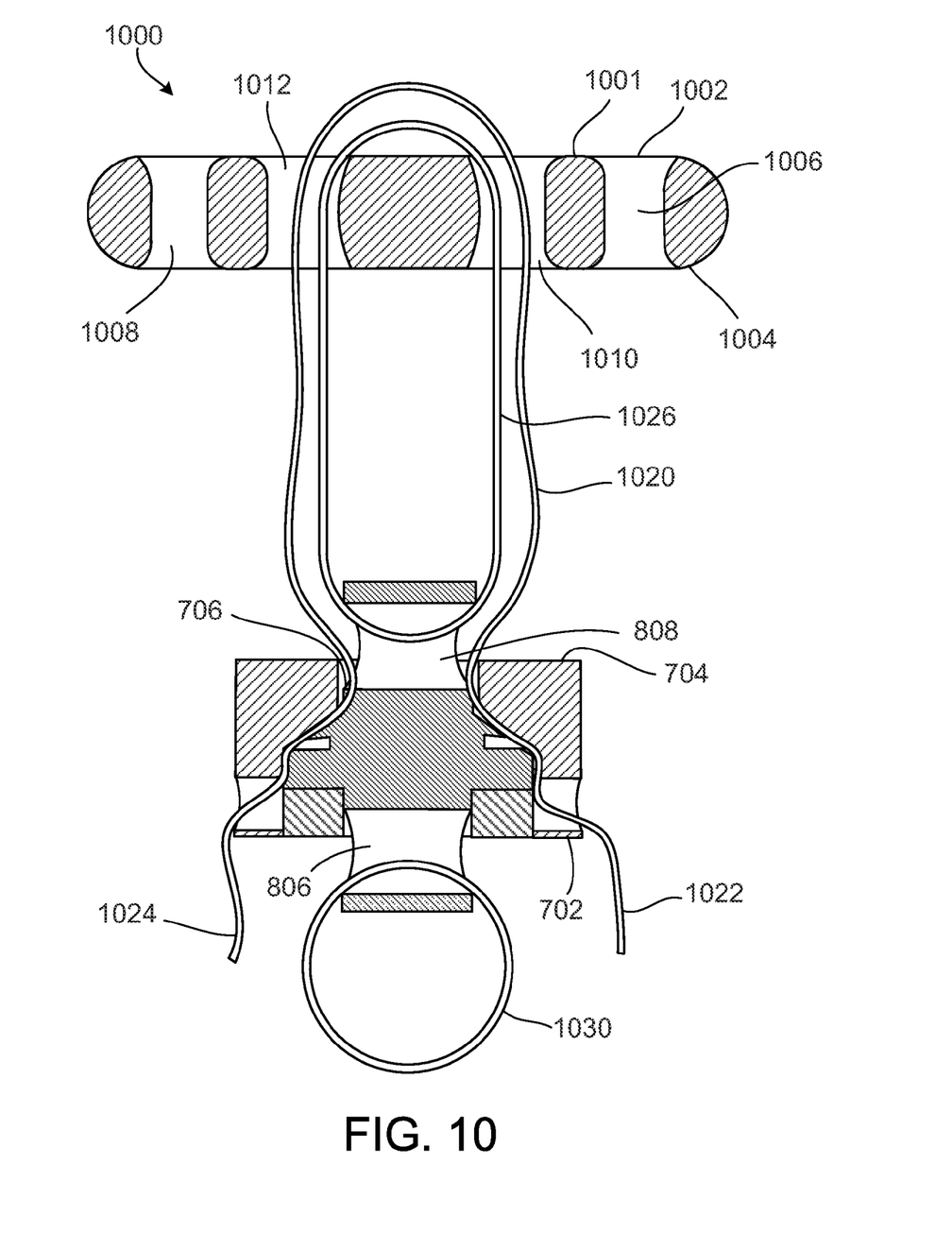
FIG. 10 is a cross-sectional view of an example of a suspension device employing the bushing member of FIG. 7 and the fixation member of FIG. 8.

Referring to FIGS. 7-10, in another implementation, a suspension device 1000 can be used, for example, as the suspension device 26. The suspension device 1000 includes a bushing member 700 (FIG. 7), a fixation member 800 (FIG. 8), and a platform member 1000 (FIG. 10).

Figure 7:
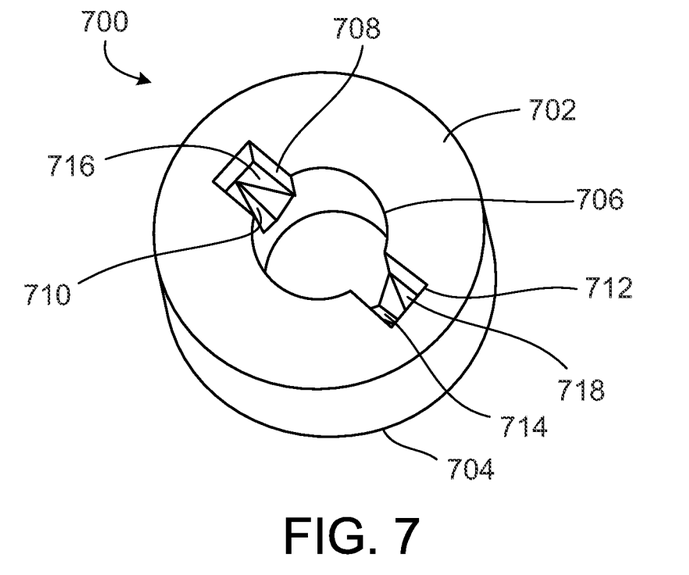
FIG. 7 is a perspective view of an example of a bushing member.

Referring particularly to FIG. 7, the bushing member 700 includes an opening 706 that spans a distance from a top surface 702 of the bushing member to a bottom surface 704. As described below, the bushing member 700 receives portions of a suture through the opening 706 such that a portion of the suture connects the bushing member 700 to the platform member 1000 (FIG. 10). The fixation member 800 (FIG. 8), configured to mate with the bushing member 700 and for attachment to a tissue graft, allows one or more portions of the suture to pass through the opening 706 in a manner that decreases a length of a portion of the suture that connects the bushing member 700 to the platform member 1000 and prevents the one or more portions of the suture to pass through the opening 706 in a manner that increases the length of the portion of the suture that connects the bushing member 700 to the platform member 1000. By doing so, the suspension device enables adjusting and maintaining a distance between the tissue graft and the suspension device.

The opening 706 is formed at a center of the top surface 702 of the bushing member 700. An axis of the opening 706 is perpendicular to the top surface 702 and the bottom surface 704, while, in other implementations, may not be perpendicular. In some implementations, the opening 706 has a circular cross-section, while in others, the opening 706 can have other cross-sections, for example, rectangular, elliptical, and the like.

The bushing member 700 includes a first recess 708 and a second recess 712 formed in the top surface 702 to receive the fixation member 800. The first recess 708 and the second recess 712 result in a first shoulder 716 and a second shoulder 718, respectively. In some implementations, the recesses are each formed on the top surface 702 adjacent to the inner surface of the opening 706, for example, on two diametrically opposite ends of the inner surface. A first groove 710 and a second groove 714 are formed within the first recess 708 and the second recess 712, respectively. In particular, the first groove 710 and the second groove 714 are partially formed on the first shoulder 716 and the second shoulder 718 within the first recess 708 and the second recess 712, respectively, and partially in the inner surface of the bushing member 700 that defines the opening 706. Each groove is tapered to receive a tapered wedge 812 and 814 formed in the fixation member 800, as described below.

FIG. 8 is a perspective view of the fixation member 800. The fixation member 800 mates with the opening 706 in the bushing member 700. The fixation member 800 includes a first passage 806 formed near a top end 802 and a second passage formed near a bottom end 804 of the fixation member 800. A size of the first passage 806 is sufficient for a suture to be passed through the first passage 806 for attachment to a tissue graft. A size of the second passage 808 is sufficient for another suture to be passed through the second passage 808 to connect the fixation member 800 mated with the bushing member 700 to the platform member 1000.

The fixation member 800 includes a retaining mechanism to selectively allow portions of a suture to pass through the opening 706. The retaining mechanism 800 includes a first wedge 812 and a second wedge 814 formed on an outer surface 810 of the fixation member 800 between the first passage 806 and the second passage 808. The first wedge 812 and the second wedge 814 engage the first recess 708 and the second recess 712, respectively, when the fixation member 800 is slid into the opening 706. In some implementations, the first wedge 812 and the second wedge 814 are formed on diametrically opposite sides of the fixation member 800 such that an axis of each of the first passage 806 and the second passage 808 are perpendicular to the axis of the fixation member 800. In addition, the axes of the passages are aligned with a straight line passing through the edges of the first wedge 812 and the second wedge 814.

Each wedge includes a tapered structure that mates with a respective groove that is partially formed in the recesses of the bushing member 700 and partially in an inner surface of the bushing member 700 that defines the opening 706. For example, starting from a flat surface 816 that faces the top end 802, the first wedge 812 tapers towards the bottom end 804. Similarly, starting from a flat surface 818 that faces the top end 802, the second wedge 814 tapers towards the bottom end 804. In some implementations, similarly to the wedges described with reference to FIG. 6, the first wedge 812 and the second wedge 814 can each include one or more step members, for example, a first step member 820 and a second step member 822, respectively.

FIG. 9 is a cross-sectional view of the fixation member 800 mated with the bushing member 700. The fixation member 800 mates with the bushing member 700 when the bottom surface 804 of the fixation member 800 is slid through the opening 706 such that the first wedge 812 and the second wedge 814 align with the first groove 710 and the second groove 714, respectively. The tapered wedges prevent the fixation member 800 from sliding out of the opening 706. In addition, a length of the fixation member 800 is greater than a height of the bushing member 700 such that at least a portion of the first passage 806 extends beyond the top surface 702 of the bushing member 700 and at least a portion of the second passage 808 extends beyond the bottom surface 704 of the bushing member 700 to permit inserting one or more portions of sutures into the respective passages after sliding the fixation member 800 through the opening 706.

In some situations, the portions of the suture for attachment to the tissue graft can be pre-loaded in the fixation member 800. In other words, the portions of the suture can be inserted into the passage 806 and formed into a loop prior to packaging. The loop may be formed as a continuous loop.

FIG. 10 is a cross-sectional view of the suspension device 1000 and sutures. FIG. 10 shows the bushing member 700 mated to the fixation member 800. The mated bushing member 700 and the fixation member 800 are connected to a platform member 1001 by portions of a suture 1020. The platform member 1001 includes multiple openings (a first opening 1006, a second opening 1008, a third opening 1010, and a fourth opening 1012). The platform member 1001 can be secured to the femoral cortex using the first opening 1006 and the second opening 1008. As described below, the platform member 1001 can be connected to the fixation member 800 by passing portions of the suture 1020 through the third opening 1010 and the fourth opening 1012.

To load the suture 1020, the suture 1020 is inserted into the opening 706 at the top surface 702 and passed out of the opening 706 at the bottom surface 704. The suture 1020 is then inserted into the first opening 1010 at the bottom surface 1004 of the platform member 1000 and passed out of the first opening 1010 at the top surface 1002. The suture 1020 is then passed into the second opening 1012 at the top surface 1002 of the platform member 1000 and passed out of the second opening 1012 at the bottom surface 1004. The fixation member 800 is then inserted into the opening 706 as described above with reference to FIG. 9. The suture 1020 is then inserted into an end of the second passage 808, which extends beyond the bottom surface 704 of the bushing member 700, and passed through the opposite end of the second passage 808. The suture 1020 is then looped through the first opening 1010 and the second opening 1012 again in a manner similar to that described above. The end of the suture 1020 that is passed out of the second opening 1012 is then inserted into the opening 706 at the top surface 704 of the bushing member 700 and passed through the opening 706 at the bottom surface.

Once loaded, the suture 1020 includes at least three portions—a first portion 1022 that passes through the first groove 710, a second portion 1024 that passes through the second groove 714, and a third portion 1026 that spans a length between the mated bushing member 700 and the fixation member 800, and the platform member 1000. When the first portion 1022 and the second portion 1024 are pulled in a direction away from the platform member 1001, the length of the third portion 1026 decreases. Alternatively, when the first portion 1022 and the second portion 1024 are held in place and a force is applied on the mated bushing member 700 and the fixation member 800 towards the platform member 1000, the length of the third portion 1026 is decreased. However, when an opposing force, i.e., a force in a direction away from the platform member 1000 is applied on the mated bushing member 700 and the platform member 800, the first wedge 812 and the second wedge 814 engage with the first groove 710 and the second groove 714, respectively, to prevent the mated bushing member 700 and the fixation member 800 from moving in a direction of the opposing force, and consequently prevent an increase in a length of the third portion 1026.

Another suture 1030 can be inserted into the first passage 806 and formed into a loop for attachment to the tissue graft (not shown). When the mated bushing member 700 and the fixation member 800 are positioned at a desired distance from the platform member 1000, and the tissue graft is attached to the loop formed using the other suture 1030, the distance between the tissue graft and the platform member 1000 can be maintained.

In operation, a surgeon can attach the loop formed using the suture 1030 to the tissue graft, and adjust the length of the third portion 1026 by pulling either the first portion 1022 or the second portion 1024 or both away from the platform member 1000 in a manner that decreases the length of the third portion 1026. Specifically, the surgeon can pass the platform member 1000, the sutures, the bushing member 700, and the fixation member 800 through the bone passage, and then pull the first portion 1022 or the second portion 1024 or both.

While this document contains many specific implementation details, these should not be construed as limitations on the scope of any implementations or of what may be claimed, but rather as descriptions of features specific to particular implementations of particular implementations. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular implementations of the subject matter have been described. Other implementations are within the scope of the following claims.

What is claimed is:

1. A tissue graft suspension device comprising:
    a platform member defining an opening;
    a suture having a first portion and a second portion, the first portion and the second portion passing through the opening such that a third portion of the suture forms a loop for attachment to a tissue graft; and
    a fixation member mating with the opening in the platform member, the fixation member including a retaining mechanism configured to allow the first portion or the second portion of the suture to pass through the opening in a manner that decreases a size of the loop while preventing the first portion or the second portion of the suture from passing through the opening in a manner that increases a size of the loop when the fixation member and the platform member are in a locked position,
    wherein the retaining mechanism includes a first wedge and a second wedge,
    the platform member includes a first groove and a second groove, the first portion of the suture passes through the first groove and the second portion of the suture passes through the second groove, and wherein the platform member further includes a second opening and a third opening, each to receive a respective end of the first and the second portions of the suture that is passed through the opening,
    the first wedge engages with the first groove such that the first portion of the suture is able to move in a first direction that decreases the size of the loop but is prevented from moving in a direction opposite the first direction to increase the size of the loop, and
    the second wedge engages with the second groove such that the second portion of the suture is able to move in a second direction that decreases the size of the loop but is prevented from moving in a direction opposite the second direction to increase the size of the loop.

2. The device of claim 1, wherein the fixation member is configured to slide through the opening in the platform member.

3. The device of claim 1, wherein the first wedge and the second wedge each include a tapered structure.

4. The device of claim 1, wherein the first wedge and the second wedge each include at least one step member.

5. The device of claim 1, wherein:
    the first wedge and the second wedge are at a first end of the fixation member;
    a passage is at a second end of the fixation member opposite from the first end; and
    the first portion of the suture and the second portion of the suture pass through the passage such that a force exerted on the loop causes the first wedge to further engage the first groove and the second wedge to further engage the second groove.

6. The device of claim 5, wherein a length of the fixation member is greater than a thickness of the platform member such that the passage at the second end extends beyond a bottom surface of the platform member.

7. A method of securing a tissue graft, the method comprising:
    providing a platform member defining an opening and having a suture attached thereto, the suture having a first portion and a second portion, the first portion and the second portion passing through the opening such that a third portion of the suture forms a loop for attachment to a tissue graft;
    providing a fixation member to mate with the opening in the platform member, the fixation member including a retaining mechanism configured to allow the first portion or the second portion of the suture to pass through the opening in a manner that decreases a size of the loop while preventing the first portion or the second portion of the suture from passing through the opening in a manner that increases a size of the loop when the fixation member and the platform member are in a locked position;
    attaching the loop to the tissue graft; and
    adjusting the size of the loop by pulling the first portion or the second portion through the opening in the manner that decreases the size of the loop,
    wherein the retaining mechanism includes a first wedge and a second wedge,
    the platform member includes a first groove and a second groove, the first portion of the suture passes through the first groove and the second portion of the suture passes through the second groove, and wherein the platform member further includes a second opening and a third opening, each to receive a respective end of the first and second portions of the suture that is passed through the opening,
    the first wedge engages with the first groove such that the first portion of the suture is able to move in a first direction that decreases the size of the loop but is prevented from moving in a direction opposite the first direction to increase the size of the loop, and
    the second wedge engages with the second groove such that the second portion of the suture is able to move in a second direction that decreases the size of the loop but is prevented from moving in a direction opposite the second direction to increase the size of the loop.

8. The method of claim 7 comprising passing the platform member, the suture, the fixation member, and attached tissue graft through a bone passage, followed by adjusting the size of the loop.

* * * * *